United States Patent

Ito et al.

[11] Patent Number: 5,095,022
[45] Date of Patent: Mar. 10, 1992

[54] PIPERIDINE DERIVATIVES AND PHARMACEUTICAL COMPOSITIONS COMPRISING THE SAME

[75] Inventors: Yasuo Ito, Katsuyama; Hideo Kato, Fukui; Eiichi Koshinaka, Katsuyama; Nobuo Ogawa, Katsuyama; Hiroyuki Nishino, Katsuyama; Jun Sakaguchi, Katsuyama, all of Japan

[73] Assignee: Hokuriku Pharmaceutical Co., Ltd., Katsuyama, Japan

[21] Appl. No.: 538,085

[22] Filed: Jun. 13, 1990

[30] Foreign Application Priority Data

Jul. 4, 1989 [JP] Japan ................... 1-171090
Apr. 9, 1990 [JP] Japan ................... 2-92194

[51] Int. Cl.$^5$ .................. A61K 31/445; C07D 403/04
[52] U.S. Cl. ............................ 514/320; 514/325; 546/196; 546/203
[58] Field of Search ............... 546/196, 203; 514/320, 514/325

[56] References Cited

U.S. PATENT DOCUMENTS 3,470,188  9/1969  Kaiser et al. ................ 546/196 X
4,826,853  5/1989  Piwinski et al. ............... 514/290

FOREIGN PATENT DOCUMENTS 235173  2/1987  Czechoslovakia .
2256392  5/1973  Fed. Rep. of Germany .

*Primary Examiner*—Mary C. Lee
*Assistant Examiner*—Jacqueline Haley
*Attorney, Agent, or Firm*—Oblon, Spivak, McClelland, Maier & Neustadt

[57] ABSTRACT

A piperidine derivative represented by the following general formula (I):

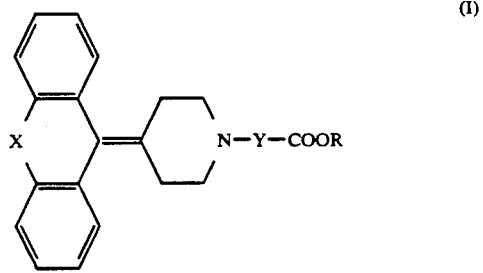

(I)

wherein R represents a hydrogen atom or a lower alkyl group; X represents —CH=CH—, —CH$_2$CH$_2$—, or —CH$_2$O—; Y represents an alkylene group having 1 to 5 carbon atoms which may be optionally substituted with a lower alkyl group, or Y represents an —A—O—B— group wherein A and B are the same or different and each independently represented an alkylene group having 1 to 3 carbon atoms which may be optionally substituted with a lower alkyl group is disclosed. Also disclosed are a pharmacologically acceptable salt of a compound of formula (I), a method for preparation of a compound of formula (I), an antihistaminic and antiallergic agent comprising a compound of formula (I), a pharmaceutical composition comprising a compound of formula (I), and a method for the treatment of an allergic disease by administering a compound of formula (I).

9 Claims, No Drawings

PIPERIDINE DERIVATIVES AND PHARMACEUTICAL COMPOSITIONS COMPRISING THE SAME

BACKGROUND OF THE INVENTION

1. Field of the Invention

The present invention relates to novel piperidine derivatives and pharmacologically acceptable salts thereof which have an antihistaminic and antiallergic activity and are useful for the treatment of, for example, bronchial asthma, allergic rhinitis, dermatosis, and urticaria, and to the method for preparation thereof.

The present invention also relates to a pharmaceutical composition comprising the effective amount of the same.

2. Description of the Prior Art

Among the piperidine compounds having a tricyclic ring substituent, for example, dibenzocycloheptene ring or a dibenzoxepine ring, in the 4-position of the piperidine ring, such compound as cyproheptadine (The Merck Index, 11th edition, 2779: 4-(5H-dibenzo[a,d]cyclohepten-5-ylidene)-1-methylpiperidine) represented by the following formula:

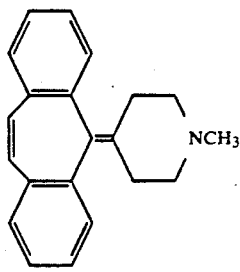

has been developed as an antihistaminic agent and is widely used clinically for the treatment of such ailments as allergic rhinitis and dermatosis.

However, this class of compounds those having a carboxyl or a lower alkoxycarbonyl group in the substituent at the 1-position of the piperidine ring have never been known to date.

A large number of antihistaminic agents have been developed so far and are used for the treatment of, for example, allergic dermatosis or rhinitis. However, adverse reactions of a central inhibitory action caused by the administration of the known antihistaminic agents such as sleepiness or sedation are found to be a great problem with these known agents. In addition, as anticholinergic action which is considered to be one of the possible reasons for hydrodipsia or mydriasis is another undesired adverse reaction of the antihistaminic agents. Various kinds of research have been conducted to solve the above problems, however, presently available antihistaminic agents are insufficient from a clinical point of view.

SUMMARY OF THE INVENTION

An object of the present invention is to provide novel compounds having an excellent antihistaminic activity as well as excellent antiallergic activity.

Another object of the present invention is to provide novel compounds which extensively eliminate undesired adverse reactions such as a central inhibitory action when administered for the treatment of such ailments as bronchial asthma, allergic rhinitis, dermatosis and urticaria.

A further object of the present invention is to provide a method for preparation of the above novel compounds. Yet another object is to provide a pharmaceutical composition comprising the novel compounds which is useful for the treatment of such ailments as bronchial asthma, allergic rhinitis, dermatosis and urticaria.

The inventors of the present invention have conducted various studies to achieve the foregoing objects and found that the objects can be effectively attained by providing novel piperidine derivatives of the present invention. These derivatives have potent antihistaminic and antiallergic activity and induce few adverse reactions such as central inhibition.

In accordance with the above objects, the present invention provides a piperidine derivative represented by the following general formula (I):

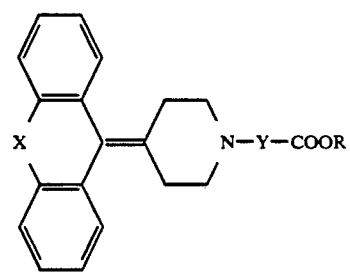

wherein R represents a hydrogen atom or a lower alkyl group; X represents $-CH=CH-$, $-CH_2CH_2-$, or $-CH_2O-$; Y represents an alkylene group having 1 to 5 carbon atoms which may be optionally substituted with a lower alkyl group, or Y represents an $-A-O-B-$ group wherein A and B are the same or different and each independently represents an alkylene group having 1 to 3 carbon atoms which may be optionally substituted with a lower alkyl group, and pharmacologically acceptable salts of the above compounds.

In accordance with another embodiment of the present invention, the present invention provides a process for preparing a piperidine derivative represented by the general formula (I). The process comprises the steps of reacting a piperidine derivative represented by the following general formula (II):

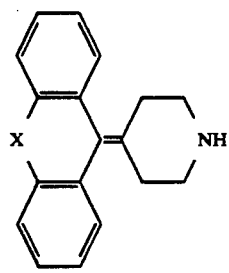

wherein X is the same as that defined above, with a compound represented by $Z-Y-COOR$ (IIIa) or $CH_2=CHCOOR$ (IIIb) wherein R and Y are the same as those defined above, and Z represents a halogen atom, in a solvent or without a solvent, and in the presence or absence of a base as a acid scavenger, followed by the step of hydrolysis in a solvent using an acid or a base, if necessary.

In accordance with yet another embodiment, the present invention provides an antihistaminic and antiallergic agent comprising an effective amount of a piperidine derivative represented by general formula (I).

In accordance with a further embodiment, the present invention provides a pharmaceutical composition for treatment of an allergic disease comprising an effective amount of a compound represented by general formula (I).

The invention also provides a method of treating an allergic disease comprising the step of administering to a mammal an effective amount of a piperidine derivative represented by general formula (I), a pharmacologically acceptable salt of the above compound, an antihistaminic and antiallergic agent comprising the same, or a pharmaceutical composition comprising the same.

Further objects, features and advantages of the present invention will become apparent from the Description of the Preferred Embodiments which follows, when read in light of the attached Examples.

DETAILED DESCRIPTION OF THE PREFERRED EMBODIMENTS

The present invention provides a piperidine derivative represented by the following general formula (I):

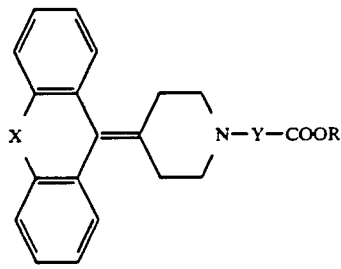

(I)

wherein R represents a hydrogen atom or a lower alkyl group; X represents —CH=CH—, —CH$_2$CH$_2$—, or —CH$_2$O—; Y represents an alkylene group having 1 to 5 carbon atoms which may be optionally substituted with a lower alkyl group, or Y represents an —A—O—B— group wherein A and B are the same or different and each independently represents an alkylene group having 1 to 3 carbon atoms which may be optionally substituted with a lower alkyl group. The present invention also provides pharmacologically acceptable salts of the above compounds. In addition, the present invention provides a process for preparing the compounds of the general formula (I), and a pharmaceutical composition comprising an effective amount of the same together with a pharmaceutically acceptable carrier or coating.

In the above general formula (I), the lower alkyl group represented by R or the lower alkyl group which may be a substituent of the alkylene group represented by Y, A, or B may be, for example, methyl, ethyl, n-propyl, isopropyl, n-butyl, isobutyl, or tert-butyl group.

Preferred examples of the present invention include:
4-(5H-dibenzo[a,d]cyclohepten-5-ylidene)-1-piperidineacetic acid;
4-(5H-dibenzo[a,d]cyclohepten-5-ylidene)-1-piperidinepropionic acid;
4-(5H-dibenzo[a,d]cyclohepten-5-ylidene)-1-piperidinebutyric acid;
4-(5H-dibenzo[a,d]cyclohepten-5-ylidene)-1-piperidinevaleric acid;
4-(5H-dibenzo[a,d]cyclohepten-5-ylidene)-1-piperidinecaproic acid;
2-[4-(5H-dibenzo[a,d]cyclohepten-5-ylidene)-piperidino]ethoxyacetic acid;
4-(10,11-dihydro-5H-dibenzo[a,d]cyclohepten-5-ylidene)-1-piperidineacetic acid;
4-(10,11-dihydro-5H-dibenzo[a,d]cyclohepten-5-ylidene)-1-piperidinepropionic acid;
4-(10,11-dihydro-5H-dibenzo[a,d]cyclohepten-5-ylidene)-1-piperidinebutyric acid;
4-(10,11-dihydro-5H-dibenzo[a,d]cyclohepten-5-ylidene)-1-piperidinevaleric acid;
4-(10,11-dihydro-5H-dibenzo[a,d]cyclohepten-5-ylidene)-1-piperidinecaproic acid;
2-[4-(5H-dibenzo[a,d]cyclohepten-5-ylidene)-piperidino]ethoxyacetic acid;
4-(dibenz[b,e]oxepin-11(6H)-ylidene)-1-piperidineacetic acid;
4-(dibenz[b,e]oxepin-11(6H)-ylidene)-1-piperidinepropionic acid;
4-(dibenz[b,e]oxepin-11(6H)-ylidene)-1-piperidinebutyric acid;
4-(dibenz[b,e]oxepin-11(6H)-ylidene)-1-piperidinevaleric acid;
4-(dibenzo[b,e]oxepin-11(6H)-ylidene)-1-piperidinecaproic acid;
2-[4-(dibenz[b,e]oxepin-11(6H)-ylidene)piperidino]ethoxyacetic acid;
ethyl 4-(5H-dibenzo[a,d]cyclohepten-5-ylidene)-1-piperidinepropionate;
methyl 2-[4-(5H-dibenzo[a,d]cyclohepten-5-ylidene)-piperidino]ethoxyacetate;
ethyl 4-(10,11-dihydro-5H-dibenzo[a,d]cyclohepten-5-ylidene)-1-piperidinepropionate;
ethyl 4-(dibenz[b,e]oxepin-11(6H)-ylidene)-1-piperidineacetate; and
methyl 2-[4-(dibenz[b,e]oxepin-11(6H)-ylidene)-piperidino]ethoxyacetate.

The compounds of the present invention represented by the above general formula (I) may be converted to pharmacologically acceptable salts, if desired, and may then be reconverted to produce the free compound from the obtained salts.

The pharmacologically acceptable salts of the compounds of the present invention represented by the general formula (I) may be acid addition salts or alkali addition salts. Examples of the acid addition salts include mineral acids such as for example hydrochloride, hydrobromide, sulfate, nitrate, and phosphate, and organic acid salt such as for example acetate, maleate, fumarate, malate, citrate, oxalate, lactate, and tartarate. Examples of the alkali addition salts include metal salts such as for example sodium, potassium, and calcium salt, and organic alkali salts such as for example ammonium salts, methylamine, ethylamine, dimethylamine, triethylamine, ethanolamine, piperidine, and piperazine salts.

The compound of the present invention represented by the above general formula (I) may have one or more asymmetric carbon atoms in the molecule, and consequently, optically active isomers and diastereoisomers may exist. These isomers as well as the racemate and the mixture of the diastereoisomers are incorporated within the scope of the present invention.

The novel piperidine derivatives of the present invention represented by the above general formula (I) can be prepared by reacting a piperidine derivative represented by the following general formula (II):

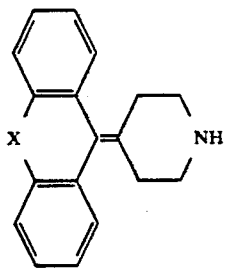

wherein X is the same as that defined above, with a compound represented by Z—Y—COOR (IIIa) or CH$_2$=CHCOOR (IIIb) wherein R and Y are the same as those defined above, and Z represents a halogen atom, in a solvent or without a solvent, and in the presence or absence of a base as a acid scavenger, followed by the step of hydrolysis in a solvent using an acid or a base, if necessary.

Any inert solvent may be used in the alkylation process of the present invention. Examples of the inert solvent include benzene, toluene, tetrahydrofuran, dioxane, acetone, acetonitrile, methanol, ethanol, isopropanol, n-butanol, dimethyl sulfoxide, and N,N-dimethylformamide.

Examples of the base used in the process of the present invention include potassium carbonate, sodium carbonate, pyridine, and triethylamine. The reaction may be carried out at from 0° to 200° C.

For the hydrolysis process, an acid such as for example hydrochloric acid or sulfuric acid, or a base such as for example sodium hydroxide, potassium hydroxide, potassium carbonate, sodium carbonate, or sodium bicarbonate may be used. A solvent used in the hydrolysis may be, for example, water, methanol, ethanol, acetone, or tetrahydrofuran, and the hydrolysis may be carried out at from 0° to 100° C.

In addition, the compounds represented by the above general formula (II), used as starting materials for the above process, are known compounds disclosed in Journal of Medicinal Chemistry, 8, 829 (1965) and the Japanese Unexamined Patent Publication No. 18478/1975, which can be readily prepared by the following process:

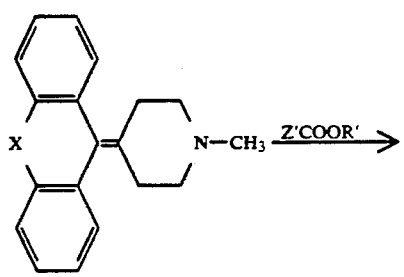

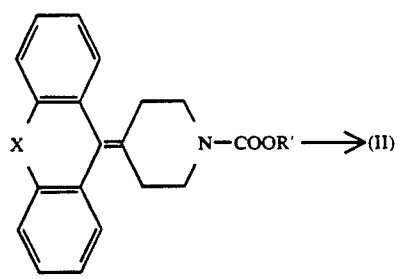

wherein, X represents the same as that defined above, Z' represents a halogen atom, and R' represents a lower alkyl group.

The novel piperidine compound of the present invention represented by the above general formula (I) and the pharmacologically acceptable salt thereof has an excellent antihistaminic and antiallergic activity, and thus is quite useful for the treatment of an allergic disease, such as, for example, bronchial asthma, allergic rhinitis, dermatosis, and urticaria.

The piperidine compounds of the present invention and their pharmacologically acceptable salts may be administered orally or parenterally to a patient as a pharmaceutical composition which comprises an effective amount of said compound or said salt together with a pharmaceutically acceptable carrier or coating.

The pharmaceutical composition suitable for oral administration may be, for example, tablet, capsule, powder, subtilized granule, granule, solution, or syrup. The pharmaceutical composition suitable for parenteral administration may be injection, suppository, inhalant, eye drop, nasal drop, ointment, or cataplasm. The pharmaceutically acceptable carrier or coating used for the preparation of the pharmaceutical composition may be excipient, disintegrant or agent for accelerating disintegration, binder, lubricant, coating agent, pigment, diluent, base, solubilizing agent, solubilizer, isotonicity, pH adjusting agent, stabilizer, propellant, and adhesive.

For the preparation of the pharmaceutical composition suitable for oral administration, dermal administration, or mucosal application, the coating or carrier may comprise the following: an excipient such as for example glucose, lactose, D-mannitol, starch, or crystalline cellulose; a disintegrant or an agent for accelerating disintegration such as for example carboxymethylcellulose, starch, or calcium carboxymethylcellulose; a binder such as for example hydroxypropylcellulose, hydroxypropylmethylcellulose, polyvinylpyrrolidone, or gelatin; a lubricant such as for example magnesium stearate or talc; a coating agent such as for example hydroxypropylmethylcellulose, sucrose, polyethylene glycol, or titanium oxide; a base such as for example petrolatum, liquid paraffin, polyethyleneglycol, gelatin, kaolin, glycerin, purified water, or hard fat; a propellant such as for example fron, diethylether, or compressed gas; an adhesive such as for example sodium polyacrylate, polyvinylalcohol, methylcellulose, polyisobutylene, or polybutene; or a base sheet such as for example cloth or plastic sheet. The pharmaceutical composition suitable for injection may comprise the following: a solubilizing agent or a solubilizer, e.g., distilled water for injection, saline, or propylene glycol which is useful for an aqueous composition or a composition for preparing aqueous solution before use; an isotonicity agent such as for example glucose, sodium chloride, D-mannitol, or glycerin; and a pH adjusting agent such as for example an inorganic or organic acid or an inorganic or organic base.

The dose of the pharmaceutical composition of the present invention for an adult patient may generally be from about 1 to 300 mg per day for oral administration, which may be increased or decreased depending on the conditions of the patient to be treated.

The present invention will be further illustrated by the following examples and reference examples. The Examples are given by way of illustration only and are not to be construed as limiting.

EXAMPLES

The following example shows the excellent effectiveness of the compounds of the present invention. The results of 48 hr homologous passive cutaneous anaphlaxis (PCA) in rats with the monitoring of antiallergic activity; and the results of potentiation of hexobarbital-induced anesthesia in mice with the monitoring of central nervous depressive activity are summarized in Table 1. The reference compound used was cyproheptadine hydrochloride.

1. 48 hr homologous passive cutaneous anaphylaxis (PCA) in rats a) Preparation of DNP-As and rat anti-DNP-As serum Ascaris extract coupled with a 2,4-dinitrophenyl group (DNP-As) was prepared by the method of Koda et al. (Folia pharmacol. japon., 78, 319-334, 1981); and anti-DNP-As containing IgE antibody serum was prepared by the method of Tada and Okumura (J. Immunol., 106, 1019-1025, 1971). The PCA titer of the antiserum was estimated to be 1:128 by 48 hr PCA in rats.

b) 48 hr homologous passive cutaneous anaphylaxis (PCA) in rats

Male Wistar rats weighing 160 to 200 g were sensitized passively by intradermal injection, in the back, of 0.05 ml of anti-DNP-As serum diluted 21-fold with saline. After 48 hr, the animals (18-20 hr fasted) were given i.v. 0.5 ml of 1% Evans blue solution containing 1 mg of DNP-As. After an additional 30 min, the animals were killed by stunning and the skins were removed. The intensity of the response was evaluated by assaying the amount of dye leaked according to the method of Katayama et al. (Microbiol. Immunol., 22, 89-101, 1978). The percent inhibition of PCA was calculated using the following formula:

$$\text{Percent inhibition} = \frac{\text{Amount of dye leaked with control} - \text{Amount of dye leaked with test compound}}{\text{Amount of dye leaked with control}} \times 100$$

Test compounds were given orally in a dose of 1 mg/kg 1 hr prior to challenge with antigen. As a control, 5 ml/kg of vehicle (0.5% CMC) alone were given in a similar manner.

The results are shown in Table 1.

2. Potentiation of hexobarbital-induced anesthesia in mice

The loss of righting reflex induced by hexobarbital was used as an index of anesthesia. Groups of eight male ddY mice (20-24 hr fasted) weighing 19 to 27 g were treated orally with the test compounds (30 mg/kg) or vehicle. Thirty min. later, 80 mg/kg of hexobarbital sodium were injected i.p. to the animals and the duration of loss of righting reflex was observed. The percent increase of sleeping time was calculated using the following formula:

$$\text{Percent increase} = \frac{\text{Sleeping time with test compound} - \text{Sleeping time with control}}{\text{Sleeping time with control}} \times 100$$

The results are listed in Table 1.

TABLE 1

| Test compound | the percent inhibition of PCA in rats (%, 1 mg/kg, p.o.) | the percent increase of hexobarbital-induced anesthesia in rats (%, 30 mg/kg, p.o.) |
|---|---|---|
| Example 1 | 71 | 106 |
| Example 21 | 91 | 29 |
| Example 22 | 81 | 37 |
| Example 23 | 81 | 51 |
| Example 24 | 87 | 75 |
| Example 25 | 78 | 80 |
| Example 26 | 59 | 22 |
| Example 28 | 89 | 83 |
| Example 29 | 94 | 45 |
| Example 30 | 91 | 53 |
| Example 31 | 59 | 36 |
| Example 32 | 77 | 15 |
| Example 33 | 91 | 39 |
| Example 34 | 69 | 31 |
| Example 35 | 85 | 76 |
| Example 36 | 54 | 34 |
| Example 37 | 85 | 49 |
| Example 38 | 83 | 41 |
| Example 39 | 78 | 80 |
| Reference compound | 47 | 203 |

The present compounds exhibited more a potent of antiallergic activity and less potent of central nervous depressive activity than the reference compound.

REFERENCE 1

Ethyl 4-(5H-dibenzo[a,d]cyclohepten-5-ylidene)-1-piperidinecarboxylate

A mixture of 33.0 g of 4-(5H-dibenzo[a,d]cyclohepten-5-ylidene)-1-methylpiperidine, 74.9 g of ethyl chlorocarbonate and 170 ml of toluene was refluxed for 3.5 hrs. After cooling, the reaction mixture was washed with hydrochloric acid and water, and then dried and concentrated. The residue was solidified by treatment with n-hexane to give 37.4 g of pale yellow crystals, which were recrystallized from ethanol to give slightly yellow needles, mp 123°-124° C.

Analysis for $C_{23}H_{23}NO_2$: Calculated C, 79.97; H, 6.71; N, 4.05. Found C, 80.24; H, 6.73; N, 3.95.

The compounds of Reference 2 to 3 were prepared in the same manner as described in Reference 1.

REFERENCE 2

Ethyl 4-(10,11-dihydro-5H-dibenzo[a,d]5-ylidene)-1-piperidine-carboxylate

Yellow liquid.
Mass spectrum m/z: 347 (M+).
IR spectrum $\nu$ (liq) cm$^{-1}$: 1700 (COO).

NMR spectrum δ (CDCl₃) ppm: 1.25(3H,t,J=7 Hz),2.36(4H,t,J=6 Hz), 2.6–3.96 (8H,m),4.14(2H,q,J=7 Hz),6.97–7.31(8H,m).

REFERENCE 3

Ethyl 4-(dibenz[b,e]oxepin-11(6H)-ylidene)-1-piperidinecarboxylate

Pale yellowish brown liquid.
Mass spectrum m/z: 349 (M+).
IR spectrum ν (liq) cm⁻¹: 1700 (COO).
NMR spectrum δ (CDCl₃) ppm: 1.25(3H,t,J=7 Hz), 2.2–4.03(8H,m), 4.14(2H,q,J=7 Hz), 4.77(1H,d,J=12 Hz), 5.69(1H,d,J=12 Hz),6.70–7.5(8H,m).

REFERENCE 4

4-(5H-dibenzo[a,d]cyclohepten-5-ylidene)piperidine

A mixture of 65.6 g of ethyl 4-(5H-dibenzo[a,d]cyclohepten-5-ylidene)-1-piperidinecarboxylate, 32.0 g of potassium hydroxide and 250 ml of n-butanol was refluxed for 2 hrs and concentrated. Water was added to the residue and extracted with toluene. The toluene layer was washed with water, dried and concentrated to give 53.2 g of pale yellow solid, which was recrystallized from methanol to give 47.9 g of colorless needles, mp 145°–147° C.

Analysis for C₂₀H₁₉N: Calculated C, 87.87; H, 7.01; N, 5.12. Found C, 87.81; H, 7.0; N, 5.07.

The compounds of Reference 5 to 6 were prepared in the same manner as described in Reference 4.

REFERENCE 5

4-(10,11-dihydro-5H-dibenzo[a,d]cyclohepten-5-ylidene)piperidine hydrochloride

Colorless plates, mp >300° C. (MeOH).
Analysis for C₂₀H₂₁N.HCl: Calculated C, 77.03; H, 7.11; N, 4.49. Found C, 77.00; H, 7.12; N, 4.47.

REFERENCE 6

4-(Dibenz[b,e]oxepin-11(6H)-ylidene)piperidine hydrochloride

Colorless prisms, mp >300° C. (EtOH).
Analysis for C₁₉H₁₉NO.HCl: Calculated C, 72.72; H, 6.42; N, 4.46. Found C, 72.72; H, 6.51; N, 4.27.

EXAMPLE 1

Ethyl 4-(5H-dibenzo[a,d]cyclohepten-5-ylidene)-1-piperidinepropionate hydrochloride A mixture of 3.01 g of 4-(5H-dibenzo[a,d]cyclohepten-5-ylidene)piperidine, 2.20 g of ethyl 3-bromopropionate, 1.52 g of potassium carbonate and 20 ml of N,N-dimethylformamide was stirred at 80° C. for 4 hrs. After cooling, water was added to the reaction mixture and then extracted with ether. The extract was washed with water, dried and concentrated to give 4.4 g of brown liquid, which was converted to the hydrochloride in the usual manner to give 4.2 g of colorless crystals. The crude hydrochloride was recrystallized from a mixture of acetone and ether to give colorless needles, mp 151°–152° C.

Analysis for C₂₅H₂₇NO₂.HCl.H₂O: Calculated C, 70.16; H, 7.07; N, 3.27. Found C, 70.26; H, 6.99; N, 3.01.

EXAMPLE 2

Methyl 2-[4-(5H-dibenzo[a,d]cyclohepten-5-ylidene)-piperidino]ethoxyacetate fumarate A mixture of 3.01 g of 4-(5H-dibenzo[a,d]cyclohepten-5-ylidene)piperidine, 2.90 g of methyl 2-chloroethoxyacetate, 2.43 g of potassium carbonate and 20 ml of N,N-dimethylformamide was stirred at 80° C. for 22 hrs. After cooling, water was added to the reaction mixture and then extracted with ether. The ether layer was extracted with aq. hydrochloric acid. The aqueous layer was made alkaline with potassium carbonate and extracted with ether. The ether layer was washed with water, dried and concentrated to give 3.16 g of yellowish brown liquid, which was converted to the fumarate in the usual manner and then recrystallized from ethanol to give pale yellow needles, mp 175°–176° C.

Analysis for C₂₅H₂₇NO₃. C₄H₄O₄: Calculated C, 68.90; H, 6.18; N, 2.77. Found C, 68.76; H, 6.22; N, 2.68.

EXAMPLE 3

Ethyl 4-(10,11-dihydro-5H-dibenzo[a,d]cyclohepten-5-ylidene)-1-piperidinebutyrate hydrochloride A mixture of 3.00 g of 4-(10,11-dihydro-5H-dibenzo[a,d]cyclohepten-5-ylidene)piperidine, 2.34 g of ethyl 4-bromobutyrate, 1.51 g of potassium carbonate and 18 ml of N,N-dimethylformamide was stirred at 70° C. for 3 hrs. After cooling, water was added to the reaction mixture and then extracted with ether. The ether layer was washed with water, dried and concentrated to give pale brown solid, which was converted to the hydrochloride in the usual manner to give 3.88 g of colorless solid. The crude hydrochloride was recrystallized from a mixture of acetone and ether to give colorless crystals, mp 182°–184° C.

Analysis for C₂₆H₃₁NO₂.HCl: Calculated C, 73.31; H, 7.57; N, 3.29. Found C, 73.27; H, 7.7; N, 3.33.

EXAMPLE 4

Ethyl 4-(dibenz[b,e]oxepin-11(6H)-ylidene)-1-piperidinepropionate

A mixture of 3.61 g of 4-(dibenz[b,e]oxepin-11(6H)-ylidene)piperidine, 2.6 g of ethyl 3-bromopropionate, 1.8 g of potassium carbonate and 25 ml of N,N-dimethylformamide was stirred at 80° C. for 2 hrs. After cooling, water was added to the reaction mixture and extracted with ether. The ether layer was washed with water and extracted with hydrochloric acid. The aqueous layer was made alkaline with potassium carbonate and extracted with ether. The ether layer was washed with water, dried and concentrated to give 4.2 g of yellowish brown liquid, which was purified by column chromatography on silica gel (eluent: chloroform) to give 3.9 g of pale yellow liquid.

Mass spectrum m/z: 377 (M+).
IR spectrum ν (liq) cm⁻¹: 1734 (COO).
NMR spectrum δ (CDCl₃) ppm: 1.25(3H,t,J=7 Hz), 1.92–2.94(12H,m), 4.13(2H,q,J=7 Hz), 4.76(1H,d,J=12 Hz), 5.72(1H,d,J=12 Hz),6.66–7.48(8H,m).

EXAMPLE 5

Ethyl 4-(dibenz[b,e]oxepin-11(6H)-ylidene)-1-piperidinevalerate hydrochloride

A mixture of 3.61 g of 4-(dibenz[b,e]oxepin-11(6H)-ylidene)piperidine, 3.00 g of ethyl 5-bromovalerate, 1.80 g of potassium carbonate and 25 ml of N,N-dimethylformamide was stirred at 80° C. for 2 hrs. After cooling, water was added to the reaction mixture and extracted with ether. The ether layer was washed with water, dried and concentrated to give 5.40 g of brown liquid, which was converted to the hydrochloride in the usual manner to give 4.76 g of colorless crystals. The crude hydrochloride was recrystallized from ethanol to give colorless needles, mp 228°–230° C.

Analysis for $C_{26}H_{31}NO_3 \cdot HCl$: Calculated C, 70.65; H, 7.30; N, 3.17. Found C, 70.76; H, 7.05; N, 3.22.

The compounds of Example 6 to 19 were prepared in the same manner as described in Example 1 to 5.

EXAMPLE 6

Ethyl 4-(5H-dibenzo[a,d]cyclohepten-5-ylidene)-1-piperidineacetate

Pale brown liquid.
Mass spectrum m/z: 359 (M+).
IR spectrum $\nu$ (liq) cm$^{-1}$: 1746 (COO).
NMR spectrum $\delta$ (CDCl$_3$) ppm: 1.24(3H,t,J=7 Hz),1.98–2.92(8H,m), 3.17(2H,s),4.16(2H,q,J=7 Hz),6.91(2H,s),7.08–7.46(8H,m).

EXAMPLE 7

Ethyl 4-(5H-dibenzo[a,d]cyclohepten-5-ylidene)-α-methyl-1-piperidineacetate hydrochloride Pale brown pillars, mp 190°–191° C. (EtOH-Et$_2$O).
Analysis for $C_{25}H_{27}NO_2 \cdot HCl$: Calculated C, 73.25; H, 6.88; N, 3.42. Found C, 73.1; H, 6.81; N, 3.31.

EXAMPLE 8

Ethyl 4-(5H-dibenzo[a,d]cyclohepten-5-ylidene)-1-piperidinebutyrate

Yellowish brown liquid.
Mass spectrum m/z: 387 (M+).
IR spectrum $\nu$ (liq) cm$^{-1}$: 1734 (COO).
NMR spectrum $\delta$ (CDCl$_3$) ppm: 1.23(3H,t,J=7 Hz), 1.56–2.8 (14H,m), 4.1(2H,q,J=7 Hz),6.9(2H,s), 7.1–7.45(8H,m).

EXAMPLE 9

Ethyl 4-(5H-dibenzo[a,d]cyclohepten-5-ylidene)-1-piperidinevalerate hydrochloride Pale yellow prisms, mp 185.5°–186.5° C. (EtOH-Et$_2$O).
Analysis for $C_{27}H_{31}NO_2 \cdot HCl$: Calculated C, 74.04; H, 7.36; N, 3.2. Found C, 74.04; H, 7.22; N, 3.14.

EXAMPLE 10

Methyl 4-(5H-dibenzo[a,d]cyclohepten-5-ylidene)-1-piperidinecaproate hydrochloride Colorless pillars, mp 200°–201° C. (EtOH).

Analysis for $C_{27}H_{31}NO_2 \cdot HCl$: Calculated C, 74.04; H, 7.36; N, 3.2. Found C, 73.82; H, 7.42; N, 3.1.

EXAMPLE 11

Ethyl 4-(10,11-dihydro-5H-dibenzo[a,d]cyclohepten-5-ylidene)-1-piperidineacetate hydrochloride Colorless crystals, mp 173°–175° C. (Me$_2$CO).
Analysis for $C_{24}H_{27}NO_2 \cdot HCl$: Calculated C, 72.44; H, 7.09; N, 3.52. Found C, 72.23; H, 7.17; N, 3.45.

EXAMPLE 12

Ethyl 4-(10,11-dihydro-5H-dibenzo[a,d]cyclohepten-5-ylidene)-1-piperidinepropionate hydrochloride Colorless needles, mp 198°–202° C. (EtOH-Et$_2$O).
Analysis for $C_{25}H_{29}NO_2 \cdot HCl \cdot \frac{1}{4} H_2O$: Calculated C, 72.10; H, 7.38; N, 3.36. Found C, 72.04; H, 7.25; N, 3.33.

EXAMPLE 13

Ethyl 4-(10,11-dihydro-5H-dibenzo[a,d]cyclohepten-5-ylidene)-1-piperidinevalerate hydrochloride Colorless crystals, mp 183.5°–185° C. (Me$_2$CO-Et$_2$O).
Analysis for $C_{27}H_{33}NO_2 \cdot HCl$: Calculated C, 73.7; H, 7.79; N, 3.18. Found C, 73.4; H, 7.75; N, 3.22.

EXAMPLE 14

Methyl 2-[4-(10,11-dihydro-5H-dibenzo[a,d]cyclohepten-5-ylidene)piperidino]ethoxyacetate Yellow liquid.
Mass spectrum m/z: 391 (M+).
IR spectrum $\nu$ (liq) cm$^{-1}$: 1758 (COO).
NMR spectrum $\delta$ (CDCl$_3$) ppm: 2.04–3.54(12H,m),2.63(2H,t,J=5.5 Hz), 3.68(2H,t,J=5.5 Hz),3.73(3H,s),4.12(2H,s),6.98–7.22(8H,m).

EXAMPLE 15

Ethyl 4-(dibenz[b,e]oxepin-11(6H)-ylidene)-1-piperidineacetate hydrochloride

Colorless needles, mp 153°–154° C. (EtOH-Et$_2$O).
Analysis for $C_{23}H_{25}NO_3 \cdot HCl \cdot \frac{1}{2} H_2O$: Calculated C, 67,56; H, 6.66; N, 3.43. Found C, 67.61; H, 6.49; N, 3.45.

EXAMPLE 16

Ethyl 4-(dibenz[b,e]oxepin-11(6H)-ylidene)-1-piperidinebutyrate hydrochloride

Colorless needles, mp 242°–244° C. (EtOH).
Analysis for $C_{25}H_{29}NO_3 \cdot HCl$: Calculated C, 70.16; H, 7.07; N, 3.27. Found C, 70.08; H, 7.04; N, 3.16.

EXAMPLE 17

Methyl 2-[4-(dibenz[b,e]oxepin-11(6H)-ylidene)piperidino]ethoxyacetate

Pale yellow liquid.
Mass spectrum m/z: 393 (M+). IR spectrum $\nu$ (liq) cm$^{-1}$: 1756 (COO). NMR spectrum $\delta$ (CDCl$_3$) ppm: 2.0–3.0 (10H,m), 3.68(2H,t,J=5.5 Hz), 3.73(3H,s),4.11(2H,s),4.76(1H,d,J=12 Hz),5.72(1H,d,J=12 Hz),6.64–7.46(8H,m).

EXAMPLE 18

Methyl 4-(10,11-dihydro-5H-dibenzo[a,d]cyclohepten-5-ylidene)-1-piperidinecaproate hydrochloride Colorless needles, mp 188°–190° C. (Me$_2$CO).
Analysis for C$_{27}$H$_{33}$NO$_2$.HCl: Calculated C, 73.7; H, 7.79; N, 3.18. Found C, 73.47; H, 7.74; N, 3.14.

EXAMPLE 19

Methyl 4-(dibenz[b,e]oxepin-11(6H)-ylidene)-1-piperidinecaproate hydrochloride

Colorless needles, mp 214°–217° C. (Me$_2$CO).
Analysis for C$_{26}$H$_{31}$NO$_3$.HCl: Calculated C, 70.65; H, 7.3; N, 3.17. Found C, 70.61; H, 7.41; N, 3.31.

EXAMPLE 20

Ethyl 4-(5H-dibenzo[a,d]cyclohepten-5-ylidene)-1-piperidinepropionate

A mixture of 4.00 g of 4-(5H-dibenzo[a,d]cyclohepten-5-ylidene)piperidine, 2.1 ml of ethyl acrylate and 20 ml of ethanol was refluxed for 1 hr and concentrated to give 5.35 g of colorless liquid. The liquid was purified by column chromatography on silica gel (eluent: chloroform) to give 5.3 g of colorless solid, which was recrystallized from n-hexane to give colorless crystals, mp 66°–67° C.

Analysis for C$_{25}$H$_{27}$NO$_2$: Calculated C, 80.4; H, 7.29; N, 3.75. Found C, 80.35; H, 7.39; N, 3.77.

EXAMPLE 21

4-(5H-Dibenzo[a,d]cyclohepten-5-ylidene)-1-piperidinepropionic acid

A mixture of 5.30 g of ethyl 4-(5H-dibenzo[a,d]cyclohepten-5-ylidene)-1-piperidinepropionate hydrochloride, 19.3 ml of 2N sodium hydroxide aqueous solution and 30 ml of methanol was refluxed for 1 hr and concentrated. Water was added to the residue, washed with ethyl acetate and adjusted to pH 4 to 5 with 10% hydrochloric acid. The precipitate was collected by filtration to give 4.47 g of pale yellow crystals, which were recrystallized from a mixture of water and N,N-dimethylformamide to give 4.23 g of pale yellow needles, mp 201°–203° C.

Analysis for C$_{23}$H$_{23}$NO$_2$.2H$_2$O: Calculated C, 72.42; H, 7.13; N, 3.67. Found C, 72.23; H, 6.94; N, 3.67.

EXAMPLE 22

2-[4-(5H-Dibenzo[a,d]cyclohepten-5-ylidene)-piperidino]ethoxyacetic acid hydrochloride A mixture of 2.56 g of methyl 2-[4-(5H-dibenzo[a,d]cyclohepten-5-ylidene)piperidino]ethoxyacetate, 6.6 ml of 2N sodium hydroxide aqueous solution and 25 ml of methanol was refluxed for 1 hr and concentrated. Water was added to the residue, adjusted to pH 2 with 10% hydrochloric acid and extracted with chloroform. The chloroform layer was washed with water, dried and concentrated to give yellowish brown liquid, which was solidified with a mixture of chloroform and ether to give 2.7 g of pale yellow amorphous solid, mp 75°–80° C.

Analysis for C$_{24}$H$_{25}$NO$_3$.HCl.H$_2$O: Calculated C, 67.05; H, 6.56; N, 3.26. Found C, 66.99; H, 6.37; N, 3.04.

EXAMPLE 23

4-(10,11-Dihydro-5H-dibenzo[a,d]cyclohepten-5-ylidene)-1-piperidinebutyric acid hydrochloride A mixture of 3.31 g of ethyl 4-(10,11-dihydro-5H-dibenzo[a,d]cyclohepten-5-ylidene)-1-piperidinebutyrate hydrochloride, 11.7 ml of 2N sodium hydroxide aqueous solution and 35 ml of methanol was refluxed for 1 hr and concentrated. Water was added to the residue, adjusted to pH 1 with 10% hydrochloric acid. The precipitate was collected by filtlation to give 2.97 g of brown solid, which was recrystallized from a mixture of ethanol and ether to give 2.48 g of colorless needles, mp 211.5°–214.5° C.

Analysis for C$_{24}$H$_{27}$NO$_2$.HCl: Calculated C, 72.44; H, 7.09; N, 3.52. Found C, 72.26; H, 7.04; N, 3.5.

EXAMPLE 24

4-(Dibenz[b,e]oxepin-11(6H)-ylidene)-1-piperidinepropionic acid

A mixture of 3.70 g of ethyl 4-(dibenz[b,e]oxepin-11(6H)-ylidene)-1-piperidinepropionate, 9.9 ml of 2N sodium hydroxide aqueous solution and 40 ml of methanol was refluxed for 30 min and concentrated. Water was added to the residue, adjusted to pH 3 with 10% hydrochloric acid. The precipitate was collected by filtration and washed with water and ether to give 3.30 g of pale yellow crystals, which were recrystallized from a mixture of water and N,N-dimethylformamide to give 2.75 g of pale yellow crystals, mp 142°–143° C.

Analysis for C$_{22}$H$_{23}$NO$_3$.2H$_2$O: Calculated C, 68.55; H, 7.06; N, 3.63. Found C, 68.82; H, 6.97; N, 3.62.

EXAMPLE 25

4-(Dibenz[b,e]oxepin-11(6H)-ylidene)-1-piperidinevaleric acid hydrochloride

A mixture of 4.20 g of ethyl 4-(dibenz[b,e]oxepin-11(6H)-ylidene)-1-piperidinevalerate hydrochloride, 14.5 ml of 2N sodium hydroxide aqueous solution and 40 ml of methanol was refluxed for 1 hr and concentrated. Water was added to the residue, adjusted to pH 2 with 10% hydrochloric acid. The precipitate was collected by filtration and washed with water and ether to give 3.92 g of colorless crystals, which were recrystallized from water to give 3.08 g of colorless prisms, mp 304°–306° C. (dec.).

Analysis for C$_{24}$H$_{27}$NO$_3$.HCl: Calculated C, 69.64; H, 6.82; N, 3.38. Found C, 69.86; H, 6.62; N, 3.53.

The compounds of Example 26 to 39 were prepared in the same manner as described in Example 21 to 25.

EXAMPLE 26

4-(5H-Dibenzo[a,d]cyclohepten-5-ylidene)-1-piperidineacetic acid hydrochloride

Pale brown needles, mp 162°–165° C. (EtOH-Et$_2$O).
Analysis for C$_{22}$H$_{21}$NO$_2$.HCl.½H$_2$O: Calculated C, 70.11; H, 6.15; N, 3.72. Found C, 70.29; H, 6.23; N, 3.51.

EXAMPLE 27

4-(5H-Dibenzo[a,d]cyclohepten-5-ylidene)-α-methyl-1-piperidineacetic acid

Pale brown pillars, mp 184°–186° C. (MeOH-Et$_2$O).
Analysis for C$_{23}$H$_{23}$NO$_2$.H$_2$O: Calculated C, 76.01; H, 6.93; N, 3.85. Found C, 76.11; H, 7.03; N, 3.87.

EXAMPLE 28

4-(5H-Dibenzo[a,d]cyclohepten-5-ylidene)-1-piperidinebutyric acid hydrochloride

Pale yellow prisms, mp 237°–239° C. (H$_2$O).
Analysis for C$_{24}$H$_{25}$NO$_2$.HCl.½ H$_2$O: Calculated C, 71.19; H, 6.72; N, 3.46. Found C, 71.46; H, 6.82; N, 3.37.

EXAMPLE 29

4-(5H-Dibenzo[a,d]cyclohepten-5-ylidene)-1-piperidinevaleric acid hydrochloride

Pale brown needles, mp 229°–230° C. (EtOH-Et$_2$O).
Analysis for C$_{25}$H$_{27}$NO$_2$.HCl: Calculated C, 73.25; H, 6.88; N, 3.42. Found C, 73.25; H, 6.84; N, 3.30.

EXAMPLE 30

4-(5H-Dibenzo[a,d]cyclohepten-5-ylidene)-1-piperidinecaproic acid hydrochloride

Pale brown prisms, mp 213°–214° C. (EtOH-Et$_2$O).
Analysis for C$_{26}$H$_{29}$NO$_2$.HCl: Calculated C, 73.66; H, 7.13; N, 3.30. Found C, 73.37; H, 7.25; N, 3.26.

EXAMPLE 31

4-(10,11-Dihydro-5H-dibenzo[a,d]cyclohepten-5-ylidene)-1-piperidineacetic acid hydrochloride Colorless crystals, mp 237.5°–239° C. (dec.) (EtOH-Et$_2$O).
Analysis for C$_{22}$H$_{23}$NO$_2$.HCl: Calculated C, 71.44; H, 6.54; N, 3.79. Found C, 71.17; H, 6.81; N, 3.80.

EXAMPLE 32

4-(10,11-Dihydro-5H-dibenzo[a,d]cyclohepten-5-ylidene)-1-piperidinepropionic acid Colorless needles, mp 189°–191° C. (DMF-H$_2$O).
Analysis for C$_{23}$H$_{25}$NO$_2$.5/2 H$_2$O: Calculated C, 70.38; H, 7.7; N, 3.57. Found C, 70.7; H, 7.4; N, 3.63.

EXAMPLE 33

4-(10,11-Dihydro-5H-dibenzo[a,d]cyclohepten-5-ylidene)-1-piperidinevaleric acid hydrochloride Colorless needles, mp 204°–206° C. (H$_2$O).
Analysis for C$_{25}$H$_{29}$NO$_2$.HCl.¼ H$_2$O: Calculated C, 72.1; H, 7.38; N, 3.36. Found C, 72.2; H, 7.19; N, 3.33.

EXAMPLE 34

2-[4-(10,11-Dihydro-5H-dibenzo[a,d]cyclohepten-5-ylidene)piperidino]-ethoxyacetic acid Colorless needles, mp 167.5°–169° C. (H$_2$O).
Mass spectrum m/z: 377 (M+).
IR spectrum ν (KBr) cm$^{-1}$: 1590 (COO−)
NMR spectrum δ (DMSO-d$_6$) ppm: 2.24–3.04(12H,m),3.14–3.56(2H,m), 3.65(2H,t,J=5.5 Hz),3.89(2H,s),6.96–7.28(8H,m).

EXAMPLE 35

4-(Dibenz[b,e]oxepin-11(6H)-ylidene)-1-piperidinebutyric acid hydrochloride

Colorless needles, mp 244°–245° C. (H$_2$O).
Analysis for C$_{23}$H$_{25}$NO$_3$.HCl: Calculated C, 69.08; H, 6.55; N, 3.5. Found C, 69.09; H, 6.5; N, 3.42.

EXAMPLE 36

2-[4-(Dibenz[b,e]oxepin-11(6H)-ylidene)piperidino]-ethoxyacetic acid hydrochloride Pale yellow crystals, mp 223°–224° C. (MeOH-Me$_2$CO).
Analysis for C$_{23}$H$_{25}$NO$_4$.HCl: Calculated C, 66.42; H, 6.30; N, 3.37. Found C, 66.25; H, 6.30; N, 3.41.

EXAMPLE 37

4-(10,11-Dihydro-5H-dibenzo[a,d]cyclohepten-5-ylidene)-1-piperidinecaproic acid hydrochloride Colorless needles, mp 215°–219° C. (EtOH).
Analysis for C$_{26}$H$_{31}$NO$_2$.HCl: Calculated C, 73.31; H, 7.57; N, 3.29. Found C, 73.32; H, 7.70; N, 3.38.

EXAMPLE 38

4-(Dibenz[b,e]oxepin-11(6H)-ylidene)-1-piperidineacetic acid

Colorless crystals, mp 132°–135° C. (H$_2$O).
Analysis for C$_{21}$H$_{21}$NO$_3$.2H$_2$O: Calculated C, 67.91; H, 6.78; N, 3.77. Found C, 67.76; H, 6.58; N, 3.68.

EXAMPLE 39

4-(Dibenz[b,e]oxepin-11(6H)-ylidene)-1-piperidinecaproic acid hydrochloride

Colorless crystals, mp 228°–231° C. (EtOH-Et$_2$O).
Analysis for C$_{25}$H$_{29}$NO$_3$.HCl: Calculated C, 70.16; H, 7.07; N, 3.27. Found C, 70.12; H, 7.15; N, 3.26.

EXAMPLE 40

4-(5H-Dibenzo[a,d]cyclohepten-5-ylidene)-1-piperidinepropionic acid

A mixture of 146 g of 4-(5H-dibenzo[a,d]cyclohepten-5-ylidene)piperidine, 73.0 g of ethyl acrylate and 500 ml of methanol was refluxed for 1 hr and then 675 ml of 2N sodium hydroxide aqueous solution was added to the reaction mixture. The reaction mixture was refluxed for 1 hr and concentrated. Water was added to the residue and adjusted to pH 4 with hydrochloric acid. The precipitate was collected by filtration to give 200 g of colorless crystals, which were recrystallized from a mixture of water and N,N-dimethylformamide to give 198 g of colorless crystals. This compound was identified by comparing its mp, IR spectrum and NMR spectrum with those of the compound of Example 21.

EXAMPLE 41

Tablets of a pharmaceutical preparation according to the present invention are prepared in the usual manner using the following constituents:

| | |
|---|---|
| Compound of the present invention | 10 mg |
| Lactose | q.s. |
| Corn starch | 34 mg |
| Magnesium stearate | 2 mg |
| Hydroxypropylmethylcellulose | 8 mg |
| Polyethyleneglycol 6000 | 0.5 mg |
| Titanium oxide | 0.5 mg |
| | 120 mg |

EXAMPLE 42

Capsules of a pharmaceutical preparation according to the present invention are prepared in the usual manner using the following constituents:

| | |
|---|---|
| Compound of the present invention | 10 mg |
| Lactose | q.s. |
| Calcium carboxymethylcellulose | 15 mg |
| Hydroxypropylcellulose | 2 mg |
| Magnesium stearate | 2 mg |
| | 100 mg |

EXAMPLE 43

Powders of a pharmaceutical preparation according to the present invention are prepared in the usual manner using the following constituents:

| | |
|---|---|
| Compound of the present invention | 20 mg |
| Lactose | q.s. |
| D-Mannitol | 500 mg |
| Hydroxypropylcellulose | 5 mg |
| Talc | 2 mg |
| | 1000 mg |

EXAMPLE 44

Injections of a pharmaceutical preparation according to the present invention are prepared in the usual manner using the following constituents:

| | |
|---|---|
| Compound of the present invention | 1 mg |
| Glucose | 50 mg |
| Hydrochloric acid | q.s. |
| Distilled water for injection | q.s. |
| | 2 ml |

EXAMPLE 45

Suppositories of a pharmaceutical preparation according to the present invention are prepared in the usual manner using the following constituents:

| | |
|---|---|
| Compound of the present invention | 5 mg |
| Hard fat | 1295 mg |
| | 1300 mg |

EXAMPLE 46

Plasters of a pharmaceutical preparation according to the present invention are prepared in the usual manner using the following constituents:

| | |
|---|---|
| Compound of the present invention | 10 mg |
| Gelatin | 1100 mg |
| Polyvinylalcohol | 250 mg |
| Methylcellulose | 100 mg |
| Glycerin | 1500 mg |
| Kaolin | 850 mg |
| Sodium polyacrylate | 50 mg |
| Polybutene | 150 mg |
| Purified water | 990 mg |
| | 5000 mg |

What is claimed is:

1. A piperidine derivative represented by the following formula (I):

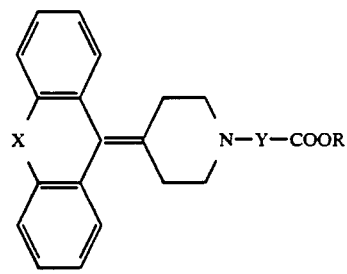

wherein R represents a hydrogen atom or a lower alkyl group; X represents $-CH=CH-$, $-CH_2CH_2-$, or $-CH_2O-$; Y represents an alkylene group having 1 to 5 carbon atoms which may be optionally substituted with a lower alkyl group, or Y represents an $-A-O-B-$ group wherein A and B are the same or different and each independently represents an alkylene group having 1 to 3 carbon atoms which may be optionally substituted with a lower alkyl group; or a pharmacologically acceptable salt of a compound of formula (I).

2. 4-(5H-dibenzo[a,d]cyclohepten-5-ylidene)-1-piperidinepropionic acid or a pharmacologically acceptable salt thereof.

3. 2-[4-(5H-dibenzo[a,d]cyclohepten-5-ylidene)-piperidino]ethoxyacetic acid or a pharmacologically acceptable salt thereof.

4. 4-(10,11-dihydro-5H-dibenzo[a,d]cyclohepten-5-ylidene)-1-piperidinepropionic acid or a pharmacologically acceptable salt thereof.

5. 4-(dibenz[b,e]oxepin-11(6H)-ylidene)-1-piperidineacetic acid or a pharmacologically acceptable salt thereof.

6. 2-[4-(dibenz[b,e]oxepin-11(6H)-ylidene)-piperidino]ethoxyacetic acid or a pharmacologically acceptable salt thereof.

7. A pharmaceutical composition for the treatment of an allergic disease comprising an effective amount of a piperidine derivative represented by the following formula (I):

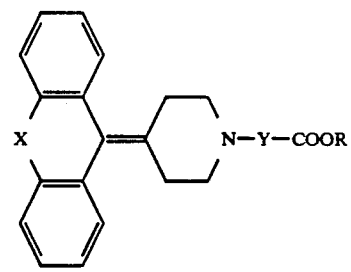

wherein R represents a hydrogen atom or a lower alkyl group; X represents $-CH=CH-$, $-CH_2CH_2-$, or $-CH_2O-$; Y represents an alkylene group having 1 to 5 carbon atoms which may be optionally substituted with a lower alkyl group, or Y represents an $-A-O-B-$ group wherein A and B are the same or different and each independently represents an alkylene group having 1 to 3 carbon atoms which may be optionally substituted with a lower alkyl group; or a pharmacologically acceptable salt of a compound of formula (I), together with a pharmaceutically acceptable carrier or coating.

8. A method for the treatment of an allergic disease comprising the step of administering to a mammal an effective amount of a substance selected from the group consisting essentially of (a) a piperidine derivative represented by the following formula (I):

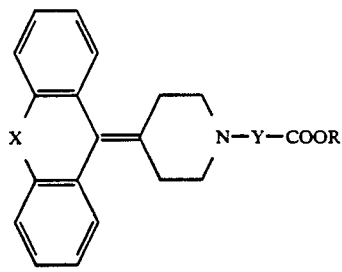

wherein R represents a hydrogen atom or a lower alkyl group; X represents —CH=CH—, —CH$_2$CH$_2$—, or —CH$_2$O—; Y represents an alkylene group having 1 to 5 carbon atoms which may be optionally substituted with a lower alkyl group, or Y represents an —A—O—B— group wherein A and B are the same or different and each independently represents an alkylene group having 1 to 3 carbon atoms which may be optionally substituted with a lower alkyl group; (b) a pharmacologically acceptable salt of a compound of formula (I); (c) an antiallergic agent comprising the compound of formula (I); or (d) a pharmaceutical composition comprising the compounds of formula (I).

9. A method according to a claim 8, wherein said step of administration is performed on a human being.

* * * * *